United States Patent [19]
Stephens et al.

[11] Patent Number: 5,522,833
[45] Date of Patent: Jun. 4, 1996

[54] RETRACTABLE OBTURATOR FOR A TROCAR

[75] Inventors: Randy R. Stephens, Fairfield; James Voegele, Cincinnati; Richard C. Smith, Loveland, all of Ohio

[73] Assignee: Ethicon Endo-Surgery, Inc., Cincinnati, Ohio

[21] Appl. No.: 297,456

[22] Filed: Aug. 29, 1994

[51] Int. Cl.⁶ ................................ A61B 17/34
[52] U.S. Cl. .......................... 606/185; 604/164
[58] Field of Search .................. 606/182, 185; 604/164, 167

[56] References Cited

U.S. PATENT DOCUMENTS

| | | | |
|---|---|---|---|
| 5,116,353 | 5/1992 | Green | 606/184 |
| 5,256,149 | 10/1993 | Banik et al. | 604/164 |
| 5,290,243 | 3/1994 | Chodorow et al. | 604/165 |
| 5,290,304 | 3/1994 | Storace | 606/184 |
| 5,312,354 | 5/1994 | Allen et al. | 604/157 |
| 5,318,580 | 6/1994 | Gresi, Jr. | 606/185 |
| 5,318,585 | 6/1994 | Guy et al. | 606/185 |
| 5,346,459 | 9/1994 | Allen | 606/185 |
| 5,352,237 | 10/1994 | Rodak et al. | 606/206 |
| 5,387,197 | 2/1995 | Smith et al. | 604/164 |
| 5,417,705 | 5/1995 | Haber et al. | 606/185 |

FOREIGN PATENT DOCUMENTS

| | | | |
|---|---|---|---|
| WO93/04632 | 3/1993 | WIPO | A61B 17/00 |
| WO93/04715 | 3/1993 | WIPO | A61M 5/178 |
| WO93/04716 | 3/1993 | WIPO | A61M 5/178 |

*Primary Examiner*—Michael H. Thaler
*Assistant Examiner*—Patrick W. Rasche
*Attorney, Agent, or Firm*—Susan M. Schmitt

[57] ABSTRACT

A retractable obturator trocar with a puncturing tip is provided. Preferably the obturator includes a safety shield covering the puncturing tip in an unarmed position and permitting the tip to extend distally from the safety shield in an armed position. The obturator preferably includes a spool retracting mechanism which causes the distally extended obturator to retract into the safety shield when a force is applied to the puncturing tip. The obturator may also be manually disengaged. The safety shield and obturator preferably extend out of the distal end of the cannula whether the trocar is armed or unarmed.

8 Claims, 7 Drawing Sheets

RETRACTABLE OBTURATOR FOR A TROCAR

FIELD OF THE INVENTION

The present invention relates to a surgical trocar and more particularly to a safety trocar which retracts into a cannula and/or safety shield after the trocar has been used to pierce tissue such as the abdominal wall of a patient.

BACKGROUND OF THE INVENTION

A trocar assembly is a surgical instrument typically comprised of a trocar obturator having a puncturing distal end and a trocar sheath or cannula which is adapted to slide over the outer diameter of the trocar obturator. The trocar obturator and cannula are used together to puncture tissue to gain access to a surgical site. Once the puncture is made the trocar obturator is adapted to be removed from the cannula thus permitting the use of operating instruments through the hollow cannula tube.

The distal end of most trocar obturators forms a sharp tip. Most available trocars have a safety shielded tip. The safety shield of these trocars generally slides proximal and distal to expose and cover the sharp tip. The safety shield will cover the tip until a force has been applied to the shield such as when the trocar assembly is being inserted through an abdominal wall. Typically, in the case of these safety shielded obturators, after the tip has pierced the abdominal wall the force is released from the shield allowing it to move distally to cover the tip in a locked position.

Other trocars have been used in which the tip moves distally and proximally in and out of the trocar cannula. The obturator tip may or may not have, in addition, a safety shield which covers the tip when the obturator is removed from the cannula. These safety shields, however do not cover the tip when the obturator is inserted in the cannula. A disadvantage of these retracting obturator trocar assemblies is the tip which remains flush within the distal end of the cannula when it is in the fully retracted position, is nonetheless exposed by the opening on the distal end of the cannula. Another disadvantage of these devices is the inability of the user to use the tip which has retracted, to reenter the abdomen through the existing puncture site. This procedure is commonly done with existing safety shield retracting trocars by locking the shield forward without first rearming the trocar and thus without exposing the sharp tip. Since the retraction mechanism in a retracting trocar obturator depends on a resistive force against the blade to trigger the blade retraction, reentry through an existing opening in the abdomen produces little resistive force against the blade raising the possibility-that the blade will not retract properly. Other known retractable trocar obturators do not provide a protective end for users when the obturator is outside of the cannula. Also, known retractable trocar obturators have bulky handles in which the retracting mechanism is typically located. This makes the trocar difficult and awkward to handle.

SUMMARY OF THE INVENTION

Accordingly, it is an object of the invention to provide an efficiently constructed and sized obturator retraction mechanism.

It is another object of the present invention to provide a retractable trocar obturator which may be used to safely reenter a puncture site. Accordingly, a preferred embodiment provides a trocar assembly with a safety shield tip fixed in a position extending beyond the distal end of the cannula so that when the obturator is unarmed, the sharp tip of the trocar is recessed and protected within the safety shield tip and the safety shield tip may be used to reenter the wound site.

It is also an object of the invention to provide a retractable trocar in which, unless armed, the sharp tip is always shielded regardless of whether the trocar is inserted through the cannula or not.

Accordingly, a trocar with a retractable obturator is provided having a housing coupled by way of an obturator shaft to a puncturing tip. The obturator includes a rotating element contained in the housing. The rotating element is coupled to the shaft. A spring biases the rotating element in a direction for proximally retracting the obturator device. An arming device is adapted to move said obturator shaft from an unarmed position to an armed position by rotating the rotating element in a direction which extends the obturator distally. A safety shield covers the obturator in the unarmed position and permits the tip to extend distally from safety shield in the armed position, A stop is included for locking the obturator in the armed position. The stop is released by a stop release when a force is applied to the puncturing tip in a proximal direction. Thereafter the rotating element rotates to retract the obturator to move the trocar from the armed position to the unarmed position.

The rotating element may comprise a spool engageably coupled to said shaft by way of a winding material. The winding material is flexible enough to wind about said spool as said spool rotates to retract the obturator and stiff enough to translate the rotational movement of the spool into a longitudinal movement to distally extend the obturator.

Another object of the invention is to provide an arming mechanism which permits the obturator to retract independent of the retraction of the arming mechanism.

Accordingly an arming mechanism is provided which permits the obturator to retract after the arming mechanism has been actuated independent of the release or retraction of the arming mechanism. Preferably an arming button is advanced to arm the trocar. Upon advancement the arming button is disengaged from the obturator and is only reengaged when both the arming button and the obturator are fully retracted.

The trocar obturator may be adapted to be inserted through the lumen of a cannula, In a preferred embodiment the trocar obturator and protective safety shield extend distally out of the distal end of the cannula.

These and other objects of the invention will be better understood from the following Detailed Description of the Drawings when taken in conjunction with the Detailed Description of the Invention.

DETAILED DESCRIPTION OF THE DRAWINGS

Figure 1:
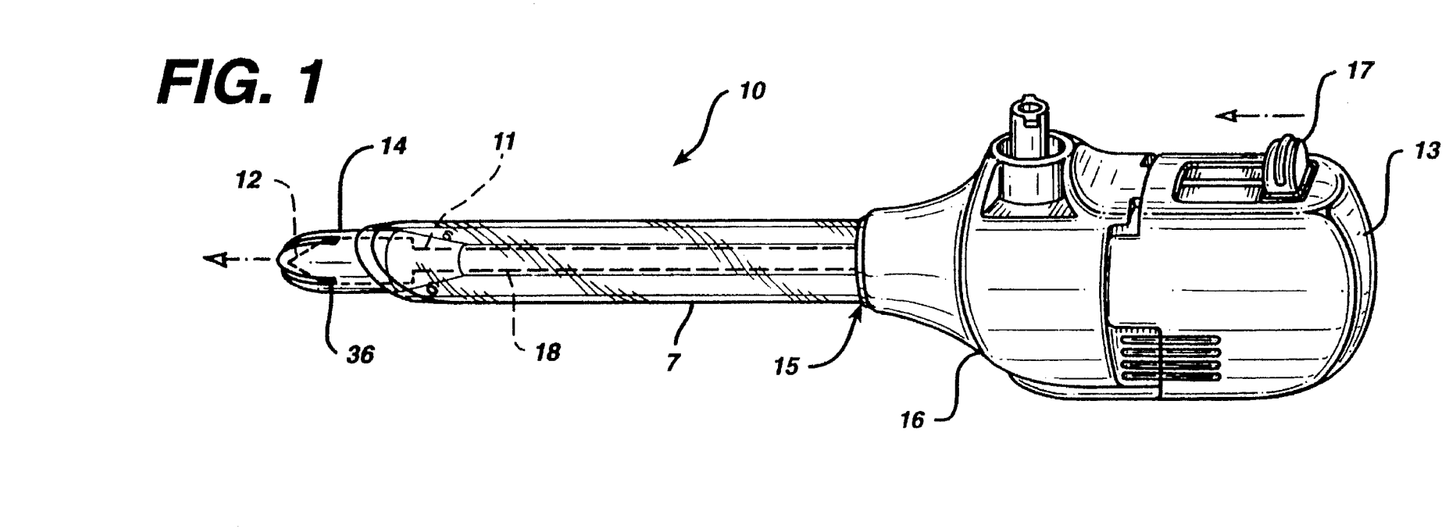
FIG. 1 is a perspective view of a trocar assembly of the present invention.
Figure 2:
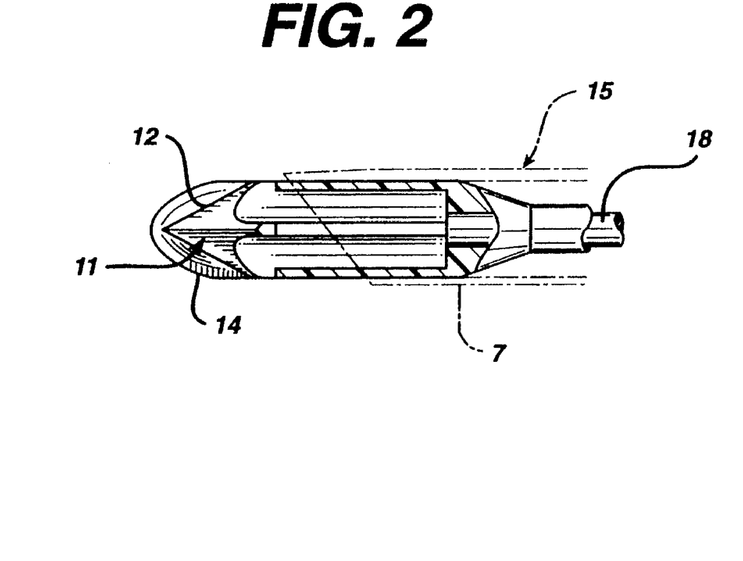
FIG. 2 is a partial cross-sectional view of the distal end of the trocar assembly illustrated in FIG. 1 with the trocar assembly in an unarmed position.
Figure 3:
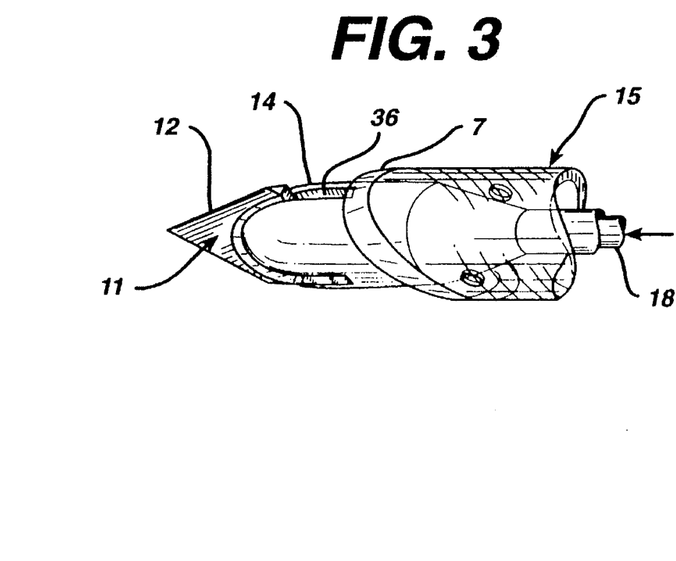
FIG. 3 is a perspective view of the distal end of the trocar assembly of the present invention in an armed position.

Referring now to FIG. 1 there is illustrated a trocar assembly of the present invention comprising a trocar obturator 11 and a cannula 15. Cannula 15 is adapted to slidably receive the trocar within a lumen extending longitudinally through the cannula. The cannula 15 includes a cannula handle 16 mounted to the cannula tube 7. The trocar obturator 11 includes a tip 12 coupled to the distal end of a shaft 18, and an obturator housing 13 coupled to the proximal end of the shaft 18. A safety shield 14 extends from the obturator housing to the distal end of the obturator, covering the obturator shaft 18 and tip 12. When inserted through the cannula 15, in an unarmed position, the trocar tip 12 and surrounding safety shield 14 extend distally of the distal end of the cannula 15. (FIG. 2) In an armed position the trocar tip 12 extends distally of the safety shield 14 through an opening 36 in the distal end of the safety shield 14. (FIG. 3)

Figure 4:
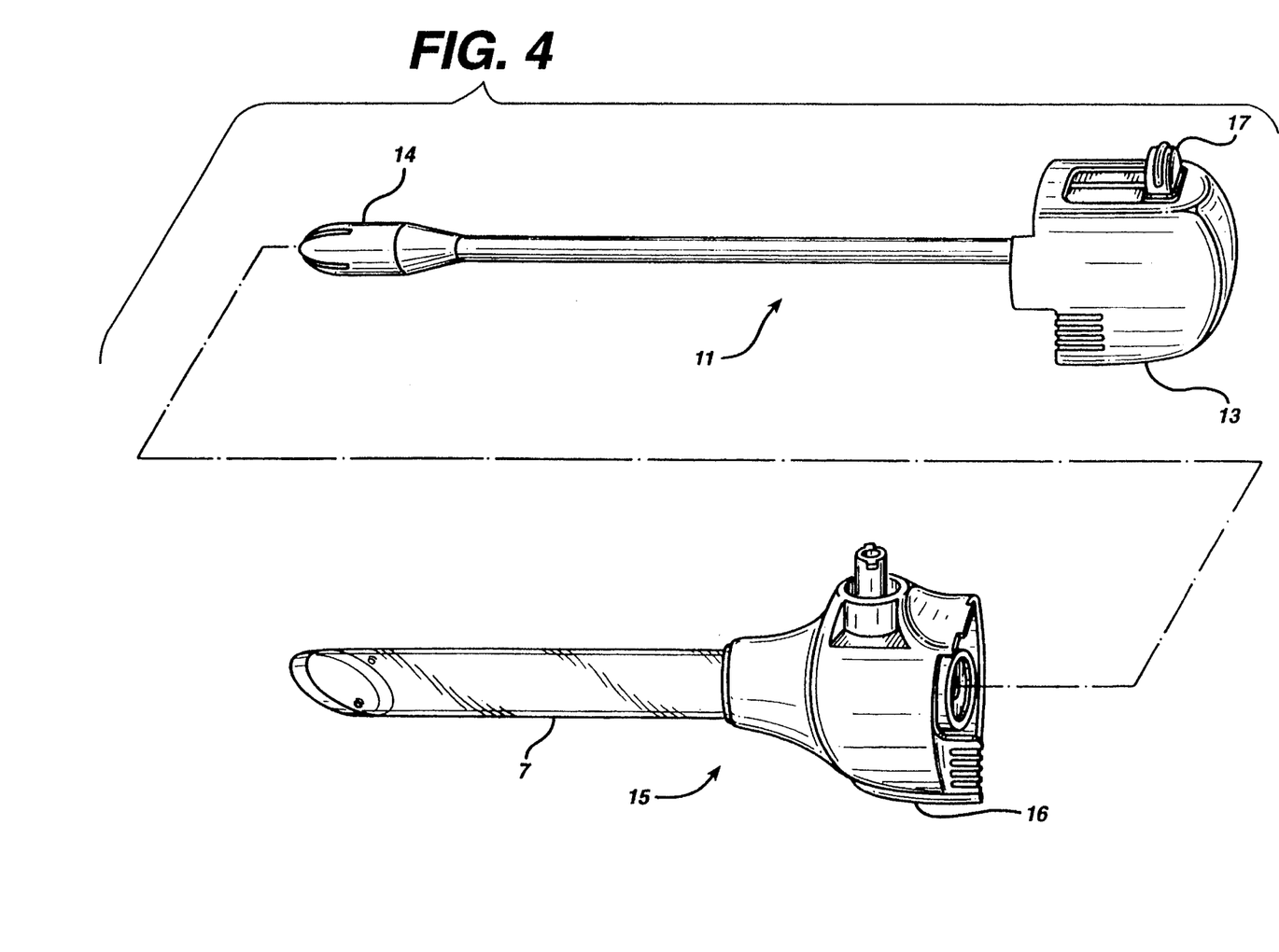
FIG. 4 is an exploded perspective view of the trocar assembly of the present invention illustrating the separable obturator and cannula portions.

FIG. 4 illustrates the two portions of the trocar assembly, the cannula 15 and the obturator 11 separated from one another. The safety shield 14 protects the tip 12 when the cannula 15 and obturator 11 are separated.

Figure 5:
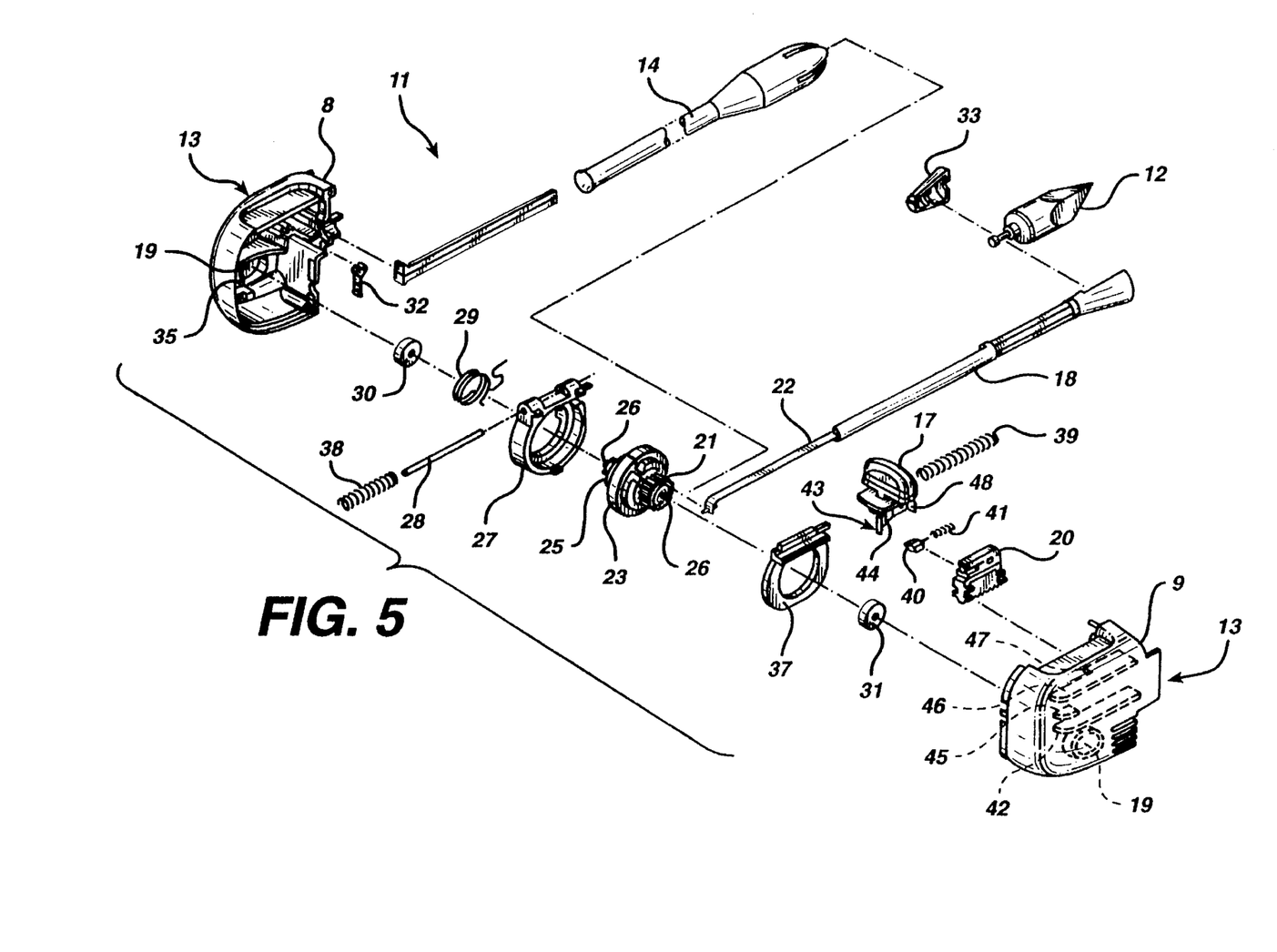
FIG. 5 is a exploded perspective view of the trocar obturator of the present invention.

FIG. 5 illustrates an exploded view of the trocar obturator 11 of the present invention. The trocar tip 12 has a pyramidal shaped sharp tip or blade on its distal end. The trocar tip 12 is coupled to the distal end of the shaft 18 and covered at its proximal end by a cap 33. The thin metal band 22 is coupled to a spool 23 and is adapted to wind around the spool 23. The spool 23 is contained in the housing 13 and includes circular pins 26 which extend axially from the circular spool 23. Pins 26 of spool 23 extend through bearing 30 on one side of the spool 23 and bearing 31 on the other side of the spool 23. Bearings 30, 31 are situated within slots 19 which are molded into each side of housing 13.

The spool 23 is housed in a spool housing 27. Spool housing cover 37 captures spool 23 within the spool housing 27. The spool housing 27 slides proximal and distal on guide pin 28. A spring 38 on guide pin 28 biases the spool 23 in a distal direction. The spool 23 includes an arming gear 21 extending axially from housing 27 on one side and first cam surface 24 and a second cam surface 25 extending axially from the other side of the housing 27. A torsion spring 29 is coupled to the spool 23 within the spool housing 27 so as to bias the spool in a counter clockwise direction. It should be noted that the direction of torsion spring bias in FIGS. 12–16 described below, is clockwise, because FIGS. 12–16 illustrate the side of the device opposite from the side illustrated in FIGS. 5–7.

Housing 13 is comprised of a first half 8 and a second half 9 which fit together to contain the parts of the arming and retracting mechanisms of the device. The first half 8 of housing 13 includes a stop 35 molded into the housing 13 and a pawl 32 which impede the rotation of spool 23 during different stages of the trocar obturator use, as will be discussed in more detail with respect to FIGS. 12–16.

Obturator housing 13 includes an arming button 17 extending from housing 13 for user arming of the trocar assembly. The arming button 17 includes a catch spring 43 which disengageably couples the arming button 17 to an arming rack 20. The arming rack 20 has teeth that engage with an arming gear 21 of the spool 23.

The second half 9 of the housing 13 includes a ridge 46 which engages with the arming button 17 to guide the movement of the arming button 17 in proximal and distal directions. The arming button 17 is biased in a proximal direction by an arming rack spring 39. The second half 9 of the housing 13 also includes a ridge 42 which engages with the rack 20 to guide the movement thereof in proximal and distal directions. The arming rack 20 also includes a reengaging button 40 biased in a proximal direction with a spring 41. A protrusion 45 formed in the second half 9 of the housing 13 extends down from the top wall of the housing. The lo protrusion 45 is adapted to engage and depress the reengaging button 40, as will be described in more detail with reference to FIGS. 8–11 below.

Figure 6:
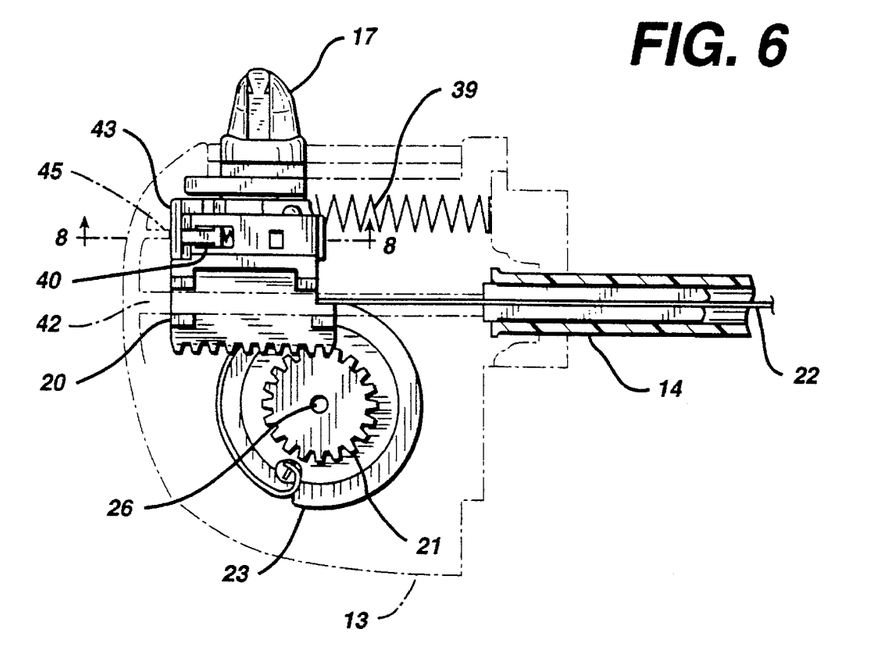
FIG. 6 is a cross-sectional side view of the handle portion of the trocar obturator illustrating the arming mechanism in an unarmed position.
Figure 7:
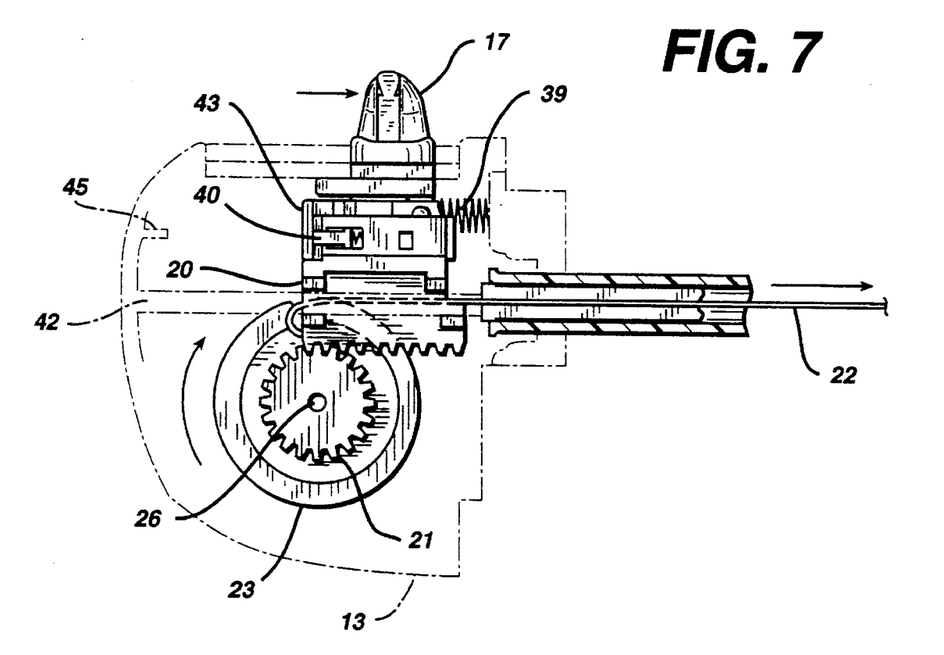
FIG. 7 is a cross-sectional side view of the handle portion of the trocar obturator illustrating the arming mechanism in an armed position.

Referring now to FIGS. 6 and 7 there is illustrated the arming mechanism of the trocar. In FIG. 6 the obturator is unarmed. In the unarmed position, the entire trocar obturator is retracted into the safety shield 14. In FIG. 7 the obturator is armed by movement of the arming button 17, in longitudinal direction towards the distal end of the trocar. The teeth of the arming rack 20 engage with the teeth of the arming gear 21. The longitudinal movement of the button 17 translates into rotational movement of the arming gear 21, and thus of the spool 23 to which the arming gear 21 is coupled. The band 22 of the obturator 11 is wrapped around the spool at the proximal end of the band 22. In FIG. 7 the band 22 is unwrapped at the proximal end by the clockwise rotational motion of the spool 23. The rotational movement of the spool 23 translates into longitudinal movement of the band 22. The band 22 is attached to the spool 23 throughout the range of motion of the band 22. The band 22 is guided through the proximal end of the safety shield 14 which directs the movement of the band 22.

Figure 8:
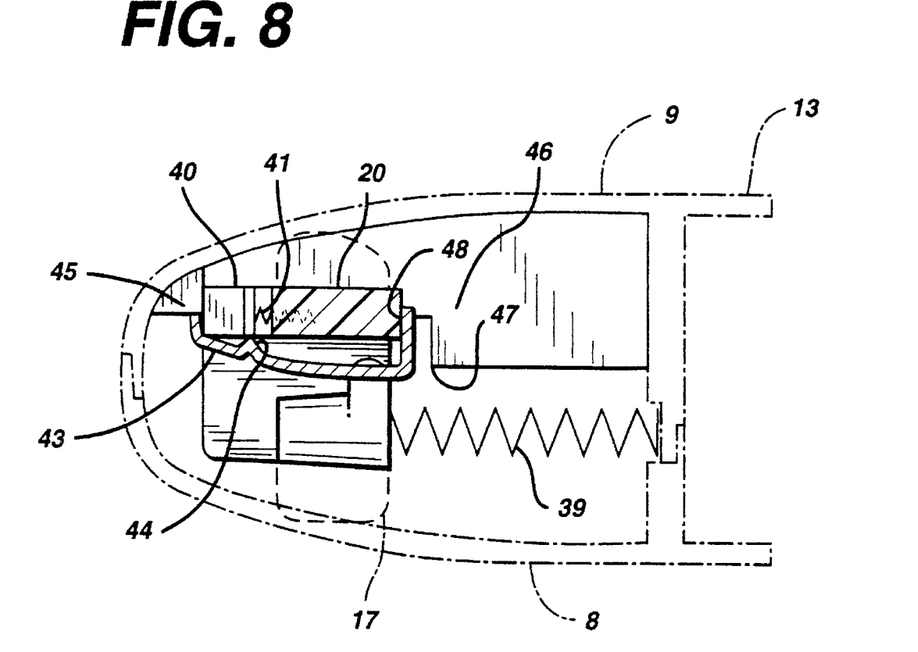
FIG. 8 is a cross-sectional front view of the handle portion illustrating the arming mechanism in an initial unarmed position.

In FIGS. 8–11, the arming mechanism is further illustrated. FIG. 8 illustrates an unarmed position, The arming button 17 and the arming rack 20 are biased in a proximal direction by spring 39 so that the protrusion 45 of the housing 13 depresses the reengagement button 40—allowing the catch spring 43 to engage the arming rack 20. Thus, when the arming button 17 as shown in FIG. 8 is depressed, the trocar may be armed.

Figure 9:
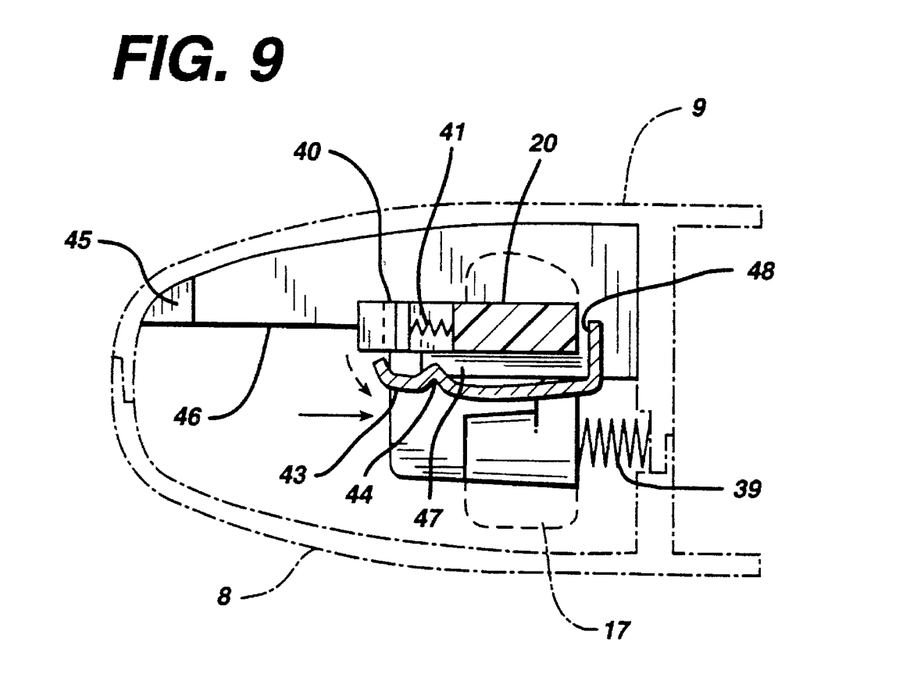
FIG. 9 is a cross-sectional front view of the handle portion illustrating the arming mechanism in an armed position after the arming button is advanced while the user continues to apply a depressive force.
Figures 12, 13:
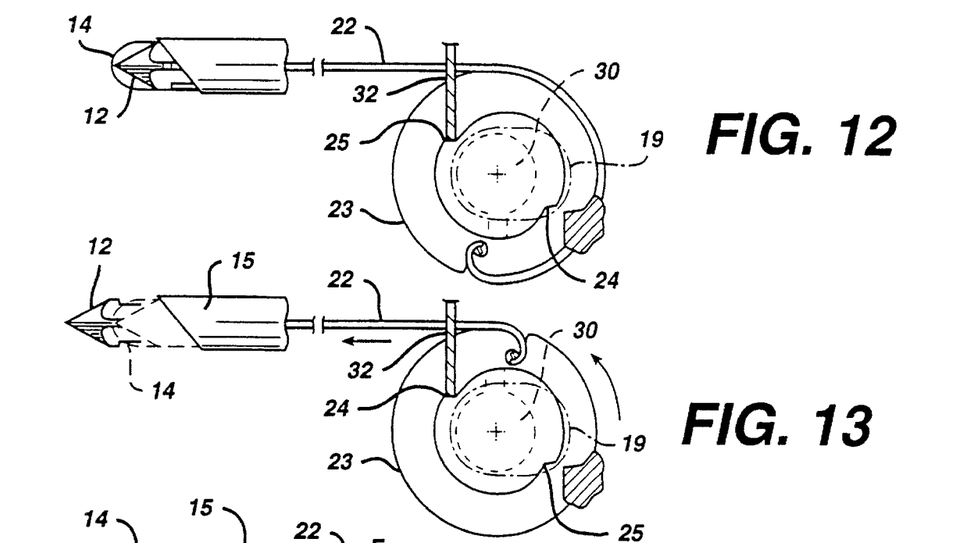
FIG. 12 is a cross-sectional side view (from side opposite of side in FIGS. 6 & 7) of the retraction mechanism and the trocar obturator tip of the present invention in an initial unarmed position.
FIG. 13 is a cross-sectional side view of the retraction mechanism and trocar obturator tip of FIG. 12 as the trocar is being armed.

FIG. 9 illustrates the arming mechanism as the arming button 17 is lo depressed and before, moving the arming button is released. As the arming button 17 is depressed, it moves along the ridge 46. A distal portion of the ridge 46 forms a protrusion 47 which catches a shelf 44 on the catch spring 43 causing the catch spring 43 to disassociate from the button 40. The catch spring shelf 48 leaves contact with the rack 20. The button 40 which no longer abuts against the protrusion 45 is biased by spring 41 to extend proximally, thereby, preventing reengagement by the catch spring 43 with the top of the rack 20. The disassociation of the catch spring 43 from the button allows the rack 20 to move with the spool 23 which is then free to rotate as shown in FIG. 13. Thus, the rack 20, which is engaged with the gear 21 that extends and retracts the obturator 11, is free to permit the obturator to retract regardless of whether or not depression of arming button 17 continues.

Figure 10:
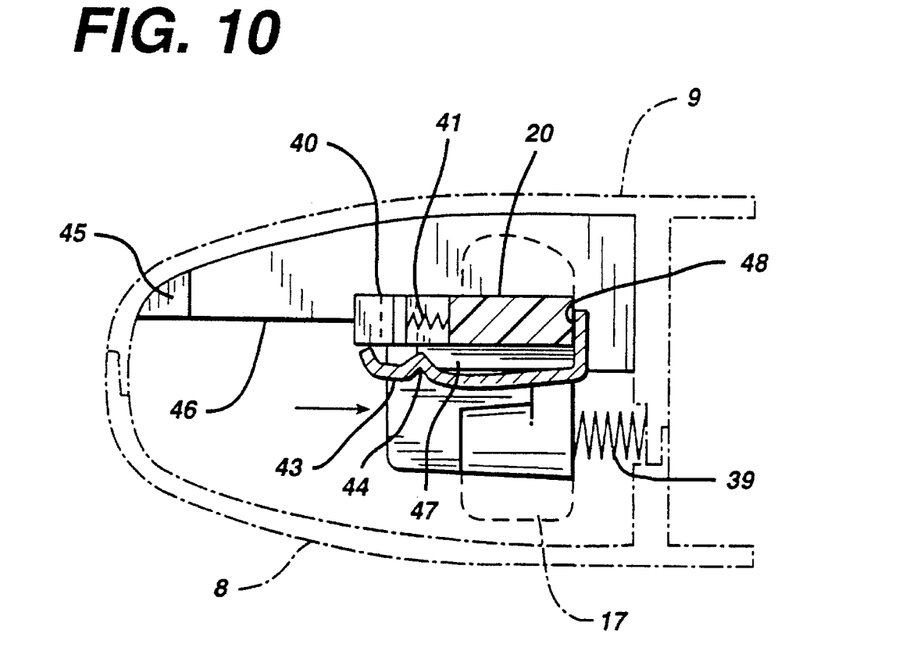
FIG. 10 is a cross-sectional front view of the handle portion illustrating the position of the arming button after the arming force has been released.

FIG. 10 illustrates the arming mechanism when the user removes the depressing force from the arming button 17. The spring 39 causes the catch spring shelf 48 to abut against the rack 20.

Figure 11:
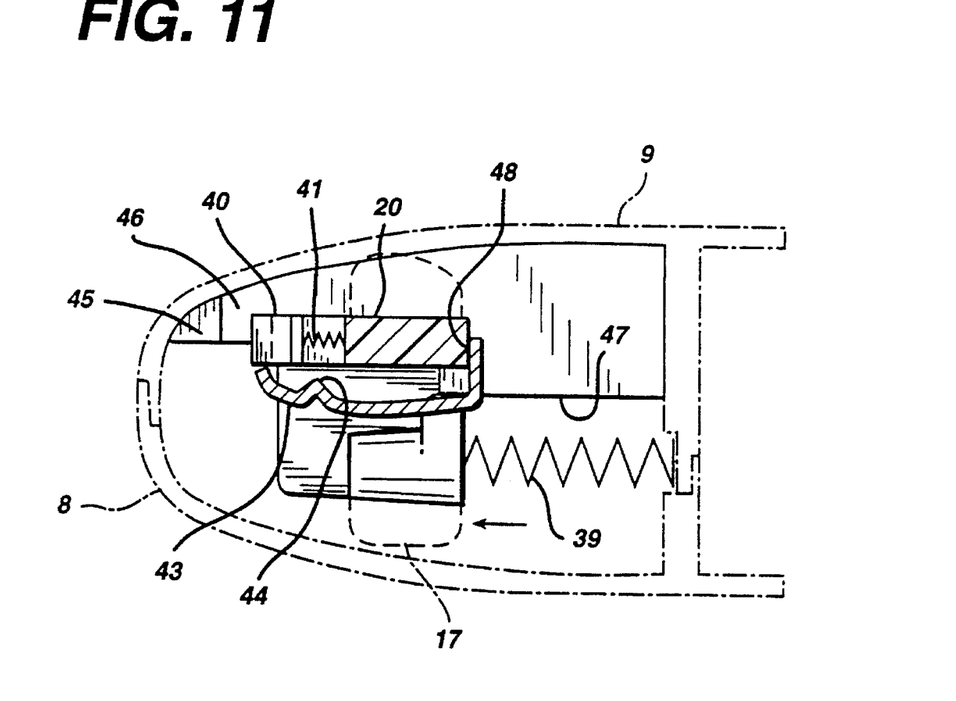
FIG. 11 is a cross sectional front view of the handle portion illustrating the arming mechanism as the obturator is retracting.

In FIG. 11, a depressing force is no longer applied to the arming button 17, and, at the same time, the obturator is retracting. The retraction of the obturator may be caused by an uplifting force on the button 17 or a force on the obturator tip 12. The arming rack 20 retracts with the obturator as described below with reference to FIGS. 12–16 and the arming button 17 retracts due to the proximal bias of spring 39. As the arming button 17 and rack 20 retract, they return to the position illustrated in FIG. 8. The reengagement button 40 is depressed as it is biased against the protrusion 45, which enables the catch spring 43 to return to its original rack engaging position so that the trocar may again be armed.

Referring now to FIGS. 12–16 the retraction mechanism of the trocar obturator is illustrated. FIG. 12 illustrates the retraction mechanism when the obturator is in an unarmed position. The pins 26 and bearings 30, 31 are situated within the slots 19 within the housing. The bearings are circular in shape and are smaller than the slot 19. Slot 19 is oval in shape and permits movement of the bearings 30, 31 in distal and proximal directions. As discussed above the spool 23 is biased in a clockwise direction, i.e., the spool tends to move in a clockwise direction. In the initial position illustrated in FIG. 12, a pawl 32 extending from the housing abuts against second cam surface 25 and prevents clockwise rotation of the spool 23. In FIG. 12, the bearings 30, 31 are situated towards the distal sides of the slots 19.

FIG. 13 illustrates the trocar obturator as it is being armed. As the arming button (FIG. 7) is advanced distally, the spool rotates in a counter clockwise direction. The band 22 unravels from the spool 23 and extends distally causing the trocar tip to extend from the safety shield 14 as illustrated in FIG. 3. The spool 23 rotates so that the pawl 32 now abuts against first cam surface 24 thereby preventing clockwise rotation of the spool 23. The bearings 30, 31 are still situated towards the distal sides of the slots 19.

Figures 14, 15, 16:
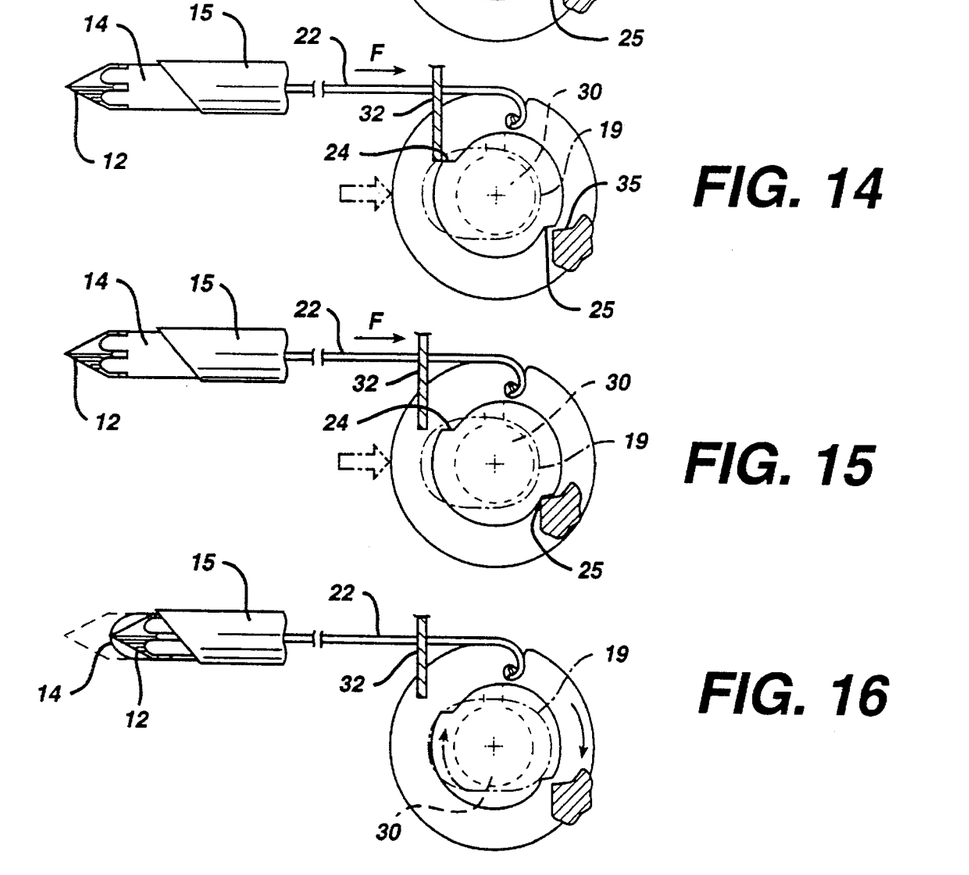
FIG. 14 is a cross-section side view of the retraction mechanism and trocar obturator tip of FIG. 12 as a force is applied to the distal end of the obturator in a proximal direction.
FIG. 15 is a cross-sectional side view of the retraction mechanism and trocar obturator tip of FIG. 12 as the force is released from trocar tip.
FIG. 16 is a cross-sectional side view of the retraction mechanism and trocar obturator tip of FIG. 12 as the trocar obturator begins to retract.

Referring to FIG. 14, the retracting mechanism is illustrated as the trocar is being used to puncture tissue to access a surgical site. The tissue provides a resistive force at the trocar tip. The force is transferred from the tip 12 through the shaft 18 and the band 22. The force causes the bearings 30, 31 to move proximally within the slot 19. The first cam surface 24 begins to move off of and disengage from the pawl 32 while the second cam surface 25 moves over the stop 35.

As is illustrated in FIG. 15, as the force continues to be applied to the trocar tip, the bearings 30, 31 continue to move proximally within the slot 19. In FIG. 15, the pawl 32 is illustrated as being disengaged from the first cam surface 24. The second cam surface 25 moves further over the stop 35. The stop 35 prevents the spool from moving clockwise by engaging with the second cam surface 25. When second cam surface 25 engages with the stop 35 and the first cam surface 24 disengages from the pawl 32, the spool rotates clockwise slightly so that when the bearings move distally again the pawl 32 will not engage the first cam surface 24.

FIG. 16 illustrates the retraction mechanism when the force on the trocar tip is released. The bearings 30, 31 are biased to move in a distal direction and to the middle of slots 19. The second cam surface 25 moves off of the stop 35. Because of the clockwise bias of the spool, the spool is then free to rotate in a clockwise direction as the first cam surface 24 is free from the pawl 32 and the second cam surface 25 is free from the stop 35. The clockwise rotation of the spool 23 retracts the band 22 and thus the trocar tip 12 which returns to its position inside of the safety shield 14. Thus, the trocar returns to the initial unarmed position illustrated in FIG. 12.

In use, the trocar obturator 11 may be transported or may be stored separately from the cannula 15, preferably with the safety shield 14 over the trocar tip 12. Alternatively the obturator 11 may be transported or stored inserted into the cannula 15. The safety shield 14 covers the tip until the trocar is armed. When ready to use the trocar obturator 11 is inserted through the cannula housing 16 and the lumen of the cannula 15. The arming button 17 is then moved distally locking the trocar tip 12 in an exposed position. The trocar remains locked into an armed position until a force has been applied to the trocar tip 12 to release the retracting mechanism or the arming button is forcibly moved in the proximal direction. For example a force is applied to the trocar handle 30 to push the trocar tip 12 through the abdominal wall of a patient. When the tip has pierced the abdominal wall, the force on the tip is released and the obturator 11 then retracts into the safety shield 14.

The retracting mechanism may be used with or without a safety shield. When used without a safety shield, the trocar tip preferably remains entirely within the cannula tube until the trocar is armed. The trocar tip is then exposed and used to puncture an abdominal wall as discussed above. In this embodiment, when the tip has punctured the wall the trocar tip retracts back into the cannula tube.

This invention has been described in connection with a surgical trocar having a retracting tip. Of course it is anticipated by this invention that the retraction mechanism may be used in other devices for similar uses such as, for example, a puncturing Verress needle.

It will be understood by those skilled in the art that various changes in modifications may be made in the invention without departing from the scope, which is defined by the following claims and their equivalents. Of course numerous applications and variations of this invention are possible.

What is claimed is:

1. A trocar with a retractable obturator comprising:

a housing coupled by way of an obturator shaft to a puncturing obturator tip;

wherein said obturator includes:

a rotating element to rotate contained in said housing, said rotating element coupled to said shaft;

a spring, said spring biasing said rotating element in a direction for proximally retracting said obturator;

an arming device adapted to move said obturator shaft from an unarmed position to an armed position, said arming device coupled to said rotating element and adapted to rotate said rotating element to extend said obturator in a distal direction;

a safety shield adapted to cover said obturator tip in said unarmed position and adapted to permit said tip to extend distally from safety shield in said armed position; and a stop for locking said obturator in said armed position, said stop being adapted to release when a force is applied to the puncturing tip in a proximal direction;

wherein said rotating element is adapted to rotate in said direction for proximally retracting said obturator to cause said obturator to move from said armed position to said unarmed position after said force is applied to said tip wherein said direction for proximally retracting said obturator includes a directional component having said proximal direction and a directional component having said distal direction.

2. A trocar with a retractable obturator comprising:

a housing coupled by way of an obturator shaft to a puncturing obturator tip;

wherein said obturator includes:

a rotating element contained in said housing, said rotating element coupled to said shaft;

a spring, said spring biasing said rotating element to rotate in a direction for proximally retracting said obturator;

an arming device adapted to move said obturator shaft from an unarmed position to an armed position, said arming device coupled to said rotating element and adapted to rotate said rotating element to extend said obturator in a distal direction;

a safety shield adapted to cover said obturator tip in said unarmed position and adapted to permit said tip to extend distally from safety shield in said armed position; and a stop for locking said obturator in said armed position, said stop being adapted to release when a force is applied to the puncturing tip in a proximal direction;

wherein said rotating element is adapted to rotate in said direction for proximally retracting said obturator, to cause said obturator to move from said armed position to said unarmed position after said force is applied to said tip; and wherein said rotating element comprises a spool, said spool coupled to said shaft by way of a winding material, said winding material adapted to wind about said spool as said spool rotates in an obturator retracting direction to retract said obturator.

3. A trocar assembly comprising:

a cannula including a cannula tube, said cannula having a lumen extending from a proximal end through a distal end;

a trocar obturator adapted to be removably inserted through said lumen of said cannula, and adapted to extend distally beyond said distal end of said cannula when inserted through said lumen;

wherein said trocar obturator comprises:

a puncturing tip coupled to an obturator shaft; and a safety shield surrounding said puncturing tip, said safety shield adapted to permit said shaft to move distally so that said puncturing tip extends distally from said safety shield from a tip covering position to a tissue puncturing position;

an obturator retractor including a rotating element coupled to said shaft;

a spring, said spring biasing said rotating element in a direction for proximally retracting said obturator; and an arming device associated with said rotating element, said arming device adapted to rotate said rotating element to extend said obturator in a distal direction and adapted to move said obturator shaft from an unarmed position to an armed position wherein said direction for proximally retracting said obturator includes a directional component having said proximal direction and a directional component having said distal direction.

4. The trocar assembly of claim 3 wherein said arming device is adapted to disassociate from said rotating element to permit independent movement of said rotating element in a direction for proximally retracting said obturator.

5. A trocar assembly comprising:

a cannula including a cannula tube, said cannula having a lumen extending from a proximal end through a distal end;

a trocar obturator adapted to be removably inserted through said lumen of said cannula, and adapted to extend distally beyond said distal end of said cannula when inserted through said lumen;

wherein said trocar obturator comprises:

a puncturing tip coupled to an obturator shaft; and a safety shield surrounding said puncturing tip, said safety shield adapted to permit said shaft to move distally so that said puncturing tip extends distally from said safety shield from a tip covering position to a tissue puncturing position;

an obturator retractor including a rotating element coupled to said shaft;

a spring, said spring biasing said rotating element in a direction for proximally retracting said obturator; and an arming device associated with said rotating element, said arming device adapted to rotate said rotating element to extend said obturator in a directional and adapted to move said obturator shaft from an unarmed position to an armed position; wherein said rotating element includes a spool adapted to rotate in a direction for proximally retracting said obturator, and adapted to rotate in an opposite direction for distally extending said obturator;

wherein said obturator retractor further comprises a band, said band coupled to said obturator shaft and to said spool;

wherein said band is adapted to wind around said spool when said spool is rotated in said obturator retracting direction for retracting said obturator; and wherein said band is adapted to translate rotational movement of said spool in said opposite direction into a distally extending movement of said obturator shaft.

6. A trocar assembly comprising:

a cannula including a cannula tube having a lumen extending therethrough;

a trocar obturator adapted to be inserted through said lumen of said cannula, said trocar obturator comprising:

a puncturing obturator tip coupled to an obturator shaft; and an obturator retractor associated with said shaft;

wherein said obturator retractor comprises:

a spool adapted to rotate in an obturator retracting direction for proximally retracting said obturator, and to rotate in an opposite direction for distally extending said obturator; and a band, said band coupled to said obturator shaft and to said spool;

wherein said band is adapted to wind around said spool when said spool is rotated in said direction for proximally retracting said obturator; and wherein said band is adapted to translate rotational movement of said spool in said opposite direction, into a distally extending movement of said obturator shaft.

7. The trocar assembly of claim 6 wherein said obturator further comprises a safety shield adapted to cover said tip in an unarmed position and adapted to permit said obturator tip to extend distally from said safety shield to an armed position.

8. A trocar assembly comprising:

a cannula including a cannula tube having a lumen extending therethrough;

a trocar obturator adapted to be inserted through said lumen of said cannula, said trocar obturator comprising:

a puncturing tip coupled to an obturator shaft; and an obturator retractor associated with said shaft;

wherein said obturator retractor comprises:

a spool;

a winding material coupled to the spool, said winding material coupled to said obturator shaft wherein said winding material is adapted to be wound around the spool as said spool rotates in a direction for proximally retracting said obturator;

a spring associated with said spool, said spring adapted to bias said spool in said direction for retracting said obturator;

a first stop associated with said spool, said stop adapted to prevent the spool from rotating in said direction for retracting said obturator, a stop release associated with said spool, said stop release adapted to release said first stop to permit said spool to rotate in said direction for retracting said obturator.

* * * * *